United States Patent
Bradway et al.

(10) Patent No.: US 10,299,797 B2
(45) Date of Patent: May 28, 2019

(54) OCCLUSION DEVICE AND METHODS OF USING THE SAME

(71) Applicant: Cook Medical Technologies LLC, Bloomington, IN (US)

(72) Inventors: Ryan Bradway, West Lafayette, IN (US); Rick Hadley, Otterbein, IN (US); Jarin Kratzberg, Lafayette, IN (US); Kimberly A. Ringenberger, Zionsville, IN (US); Kevin Wilger, Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 15/728,710

(22) Filed: Oct. 10, 2017

(65) Prior Publication Data

US 2018/0028191 A1  Feb. 1, 2018

Related U.S. Application Data

(62) Division of application No. 14/293,536, filed on Jun. 2, 2014, now abandoned.

(51) Int. Cl.
| | | |
|---|---|---|
| *A61B 17/12* | (2006.01) | |
| *A61B 17/00* | (2006.01) | |
| *A61B 90/00* | (2016.01) | |

(52) U.S. Cl.
CPC .. *A61B 17/12031* (2013.01); *A61B 17/12109* (2013.01); *A61B 17/12172* (2013.01); *A61B 2017/00853* (2013.01); *A61B 2017/00862* (2013.01); *A61B 2017/00867* (2013.01); *A61B 2017/12054* (2013.01); *A61B 2090/3966* (2016.02)

(58) Field of Classification Search
CPC ........ A61B 17/12031; A61B 17/12109; A61B 17/12172; A61B 2017/00853; A61B 2017/00862; A61B 2017/00867; A61B 2017/12054; A61B 2090/3966
See application file for complete search history.

(56) References Cited

U.S. PATENT DOCUMENTS

| | | | |
|---|---|---|---|
| 3,834,394 A | 9/1974 | Hunter | |
| 5,382,259 A | 1/1995 | Phelps | |
| 5,725,534 A | 3/1998 | Rasmussen | |
| 6,458,137 B1 | 10/2002 | Klint | |
| 8,088,103 B2 | 1/2012 | Teeslink | |
| 8,308,752 B2 | 11/2012 | Tekulve | |
| 2005/0149109 A1* | 7/2005 | Wallace | A61B 17/12022 606/200 |
| 2006/0085028 A1 | 4/2006 | Boock | |
| 2011/0213403 A1 | 9/2011 | Aboytes | |
| 2012/0303053 A1* | 11/2012 | Chen | A61B 17/12113 606/194 |

OTHER PUBLICATIONS

St. Jude Medical PDA Closure Devices brochure titled "Patient Ductus Arteriosus (PDA) Closure Devices", obtained from the Internet on Apr. 14, 2017 at: https://www.sjmglobal.com/en-int/professionals/featured-products/structural-heart/structur . . . , 3 pgs.

* cited by examiner

*Primary Examiner* — Brandy S Lee
(74) *Attorney, Agent, or Firm* — Brinks Gilson & Lione

(57) ABSTRACT

An occlusion device for occluding a body vessel and methods of using the device are disclosed.

10 Claims, 4 Drawing Sheets

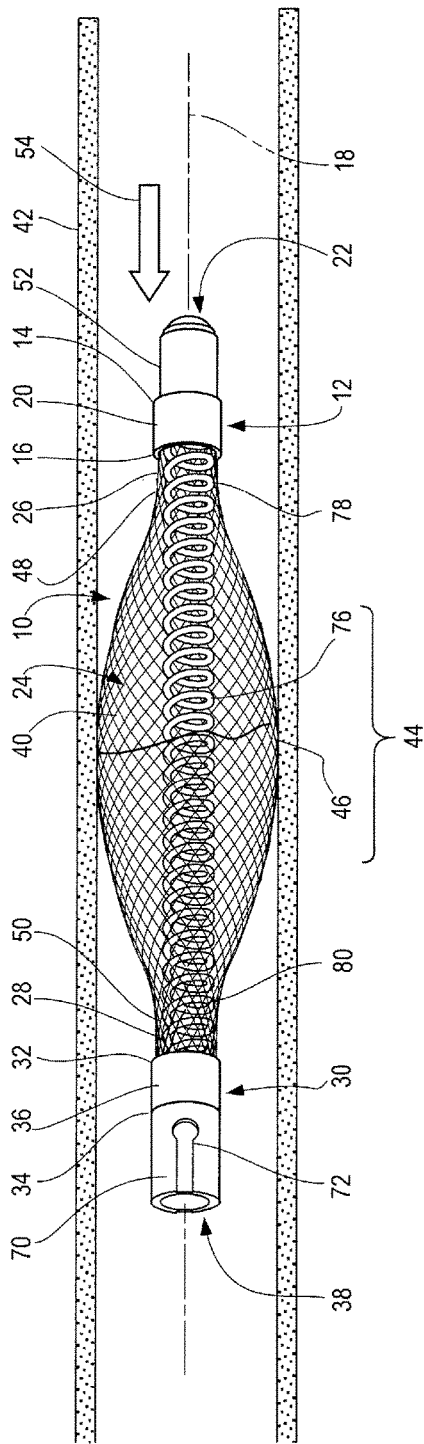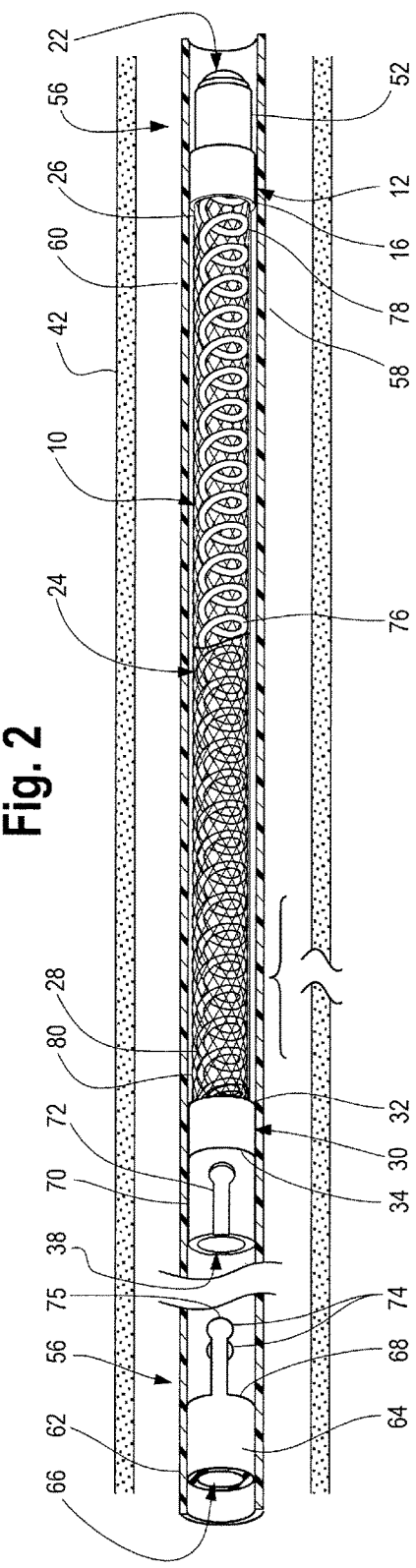

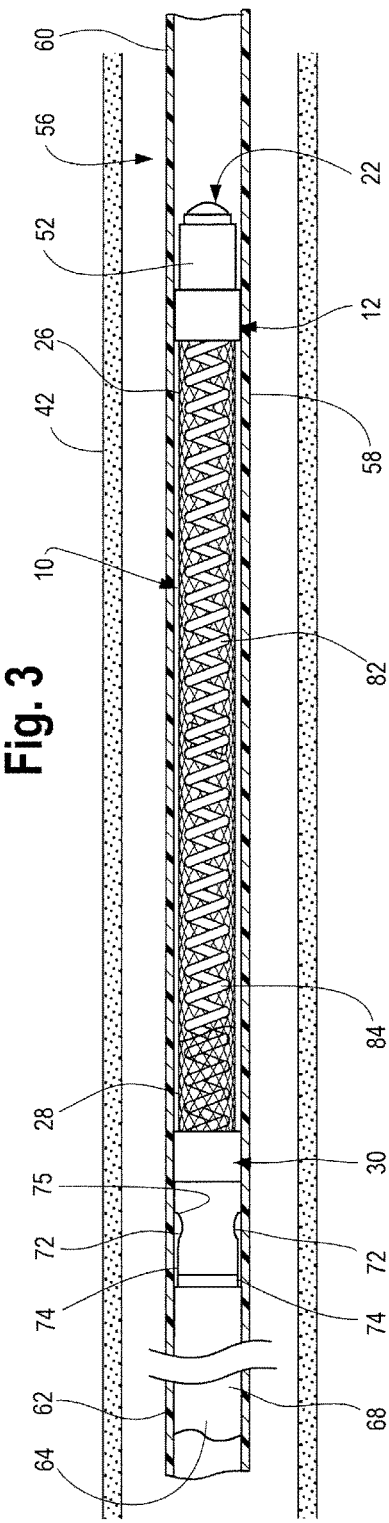
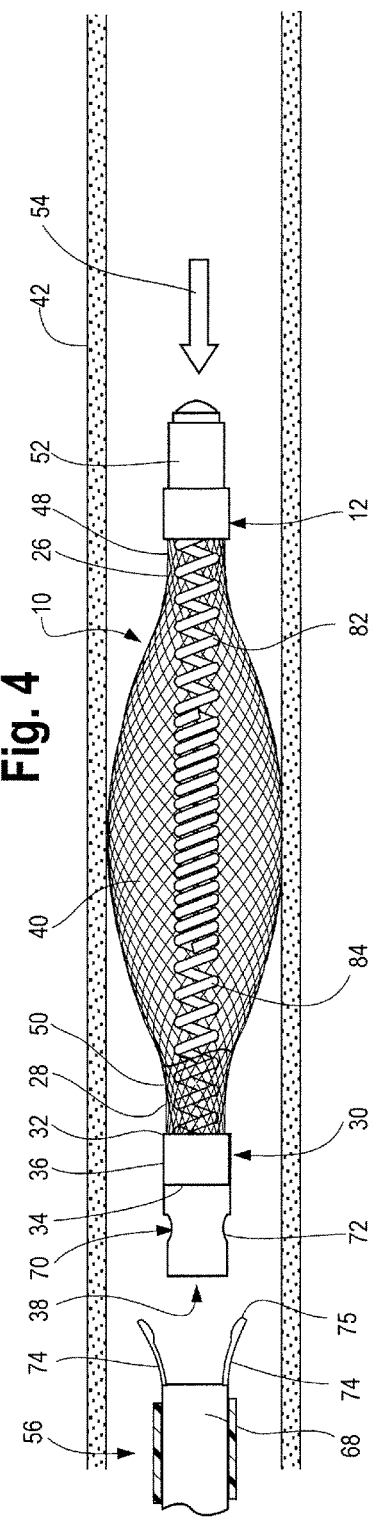

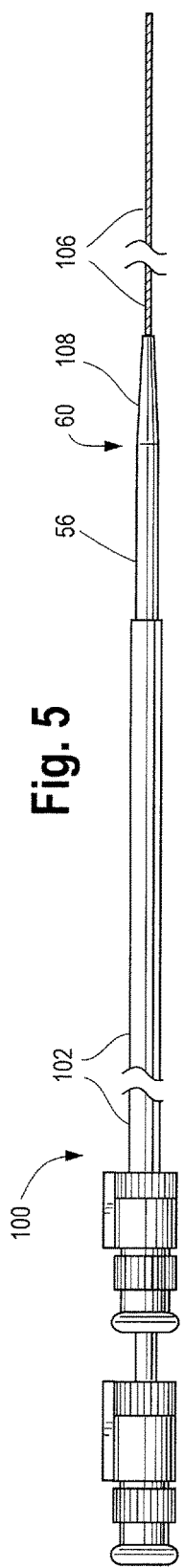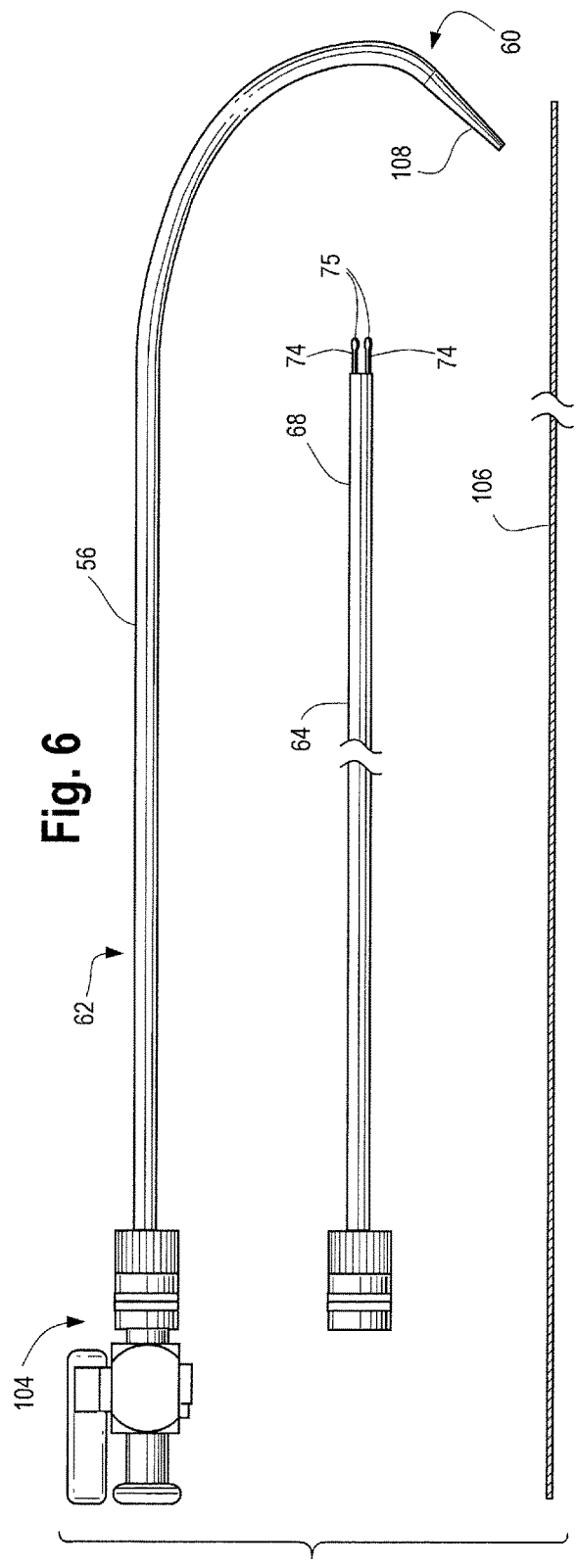

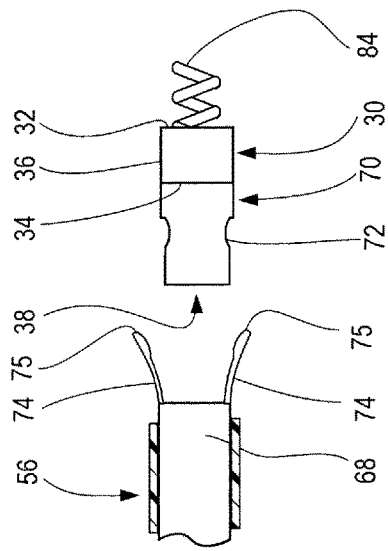
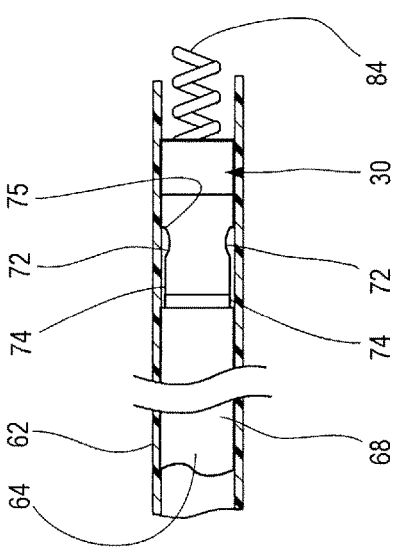

OCCLUSION DEVICE AND METHODS OF USING THE SAME

RELATED APPLICATIONS

This application is a divisional of U.S. application Ser. No. 14/293,536, filed Jun. 2, 2014, which is incorporated herein in its entirety.

BACKGROUND

The present invention generally relates to embolization or occlusion devices for the human and animal body.

An embolization or occlusion device can be placed within the lumen or interior space of an organ or physiological conduit including arteries, veins, vessels, the bilary tree, the urinary tract, the alimentary tract, the tracheobronchial tree, the genitourinary system, and the cerebral aqueduct. Occlusion devices are used for a number of different purposes, all with the common feature that it is desired to limit or stop the free flow of fluid or blood in an area of the body.

One example of an endovascular field of application for occlusion devices for percutaneous, transluminal insertion using minimally invasive techniques, is occlusion of an aneurism to prevent rupture of the vessel wall with resulting bleeding. Other applications include occlusion or treatment of varicose veins, occlusion of arteriovenous malformations (AVM), blocking of the blood flow to a tumor, and/or closure of traumatically conditioned blood flows caused by wounds, bodily injuries or gastrointestinal bleeding.

Occlusion devices can be used in many different places in the vascular system and in vessels of differing sizes and geometries. Therefore, many different occlusion devices have been designed with various basic predetermined shapes and of varying sizes. Conventionally, the predetermined shape of the occlusion device is made so that the body of the device has a diameter of the same size or slightly larger than the relevant vessel lumen, so that the body of the device exerts an abutment pressure against the vessel wall. When it is desirable to quickly occlude a blood vessel, an inflatable balloon may be temporarily used. Another example of a more permanent occlusion device includes embolization coils, which may promote blood clots or tissue growth over a period of time, thereby occluding the body cavity and/or vessel lumen. Occlusion devices having other shapes and structures may also be used as necessary or desired, including but not limited to barrels, disks, wires and/or fibers.

To deliver an occlusion device, a delivery assembly including a guidewire and a catheter may be placed transluminally in the vascular system having its distal catheter end at the site of placement. When the occlusion device leaves the distal end of the catheter, it seeks to assume a predetermined shape within the vessel or alternatively, it can be mechanically expanded within the vessel. If the size and shape of the device are deemed suitable for the vessel geometry at the site of placement, the occlusion device is disconnected from the components of the delivery assembly and the assembly removed from the vasculature.

Disclosed herein is an improved occlusion device for occluding a body lumen and/or vessel. Also disclosed is a delivery assembly and methods for placing and retrieving an occlusion device within a body vessel.

SUMMARY

In one example, an occlusion device for occluding a body lumen is disclosed. The occlusion device comprises a proximal end, a distal end spaced from the proximal end along a longitudinal axis, and an occluding member disposed between the proximal end and distal end. The occluding member has a radially-outwardly expanded configuration and a contracted configuration. At least one biasing member is disposed within the occluding member and extends between the proximal and distal ends along a longitudinal axis, the biasing member having a contracted configuration and an extended configuration. When the occlusion member is in the expanded configuration the biasing member is in the contracted position and when the occlusion member is in the contracted configuration the biasing member is in the extended position.

Another example of an occlusion device for occluding a body vessel is also disclosed. The occlusion device comprises a proximal end, a distal end spaced from the proximal end along a longitudinal axis and an occluding member disposed between the proximal end and distal end. The occluding member'has a radially-outwardly expanded configuration and a contracted configuration. A first biasing member is disposed within the occluding member having a first end adjoined to the proximal end of the device, and a second biasing member is disposed within the occluding member having a first end adjoined to the distal end of the device. The second biasing member is configured to releasably engage the first biasing member.

DESCRIPTION OF THE DRAWINGS

FIG. 1 is a partial section of a body vessel including one example of an occlusion device in a radially expanded deployed configuration therein.

FIG. 2 is a partial section of the occlusion device of FIG. 1 in a collapsed delivery configuration within an outer sheath and a distal portion of one example of a delivery assembly.

FIG. 3 is a partial section of another example of an occlusion device in a collapsed delivery configuration within an outer sheath and a distal portion of one example of a delivery assembly.

FIG. 4 is a partial section of a body vessel including another example of an occlusion device in a radially expanded deployed configuration therein.

FIG. 5 is a side view of one example of a delivery and retrieval assembly for use with an occlusion device.

FIG. 6 is an exploded view of the delivery and retrieval assembly of FIG. 5.

FIG. 7 illustrates one example of the distal end of the a delivery device engaged with the occlusion device within a delivery sheath.

FIG. 8 illustrates one example of a delivery sheath partially withdrawn and the distal end of a delivery device disengaged from the occlusion device.

DETAILED DESCRIPTION

Throughout this specification the terms "proximal" and "proximally" are used to refer to a position or direction towards the patient's heart and the terms "distal" and "distally" are used for a position or direction away the patient's heart when describing an occlusion device. In the arterial system, downstream refers to the direction further from the heart, while upstream refers to the direction closer to the heart. The terms proximal and distal, when used herein in relation to instruments used in the procedure, such as a delivery assembly, delivery device, catheter, guide wire and the like, refer to directions closer to and farther away from the operator performing the procedure. Thus, a distal end of a delivery catheter or guide wire would be farther away from the operator, while the proximal end of a delivery catheter or guide wire would be closer to the operator.

Referring now to FIG. 1, a first embodiment of an occlusion device is designated at 10. The occlusion device 10 includes a first or proximal hub 12 extending from a proximal end 14 to a distal end 16 and along a longitudinal axis 18 with a tubular wall 20 optionally defining a lumen 22. A proximal end 26 of an occluding member 24 is attached to the proximal hub 12 and extends distally therefrom for attachment at its distal end 28 to a second or distal hub 30. Distal hub 30 has a proximal end 32 and a distal end 34, with a tubular wall 36 optionally defining a second lumen 38. The occluding member 24 may define an interior volume or space 40. Preferably, at least a portion of member 24 forms an occlusive barrier when deployed within a body lumen and/or vessel 42.

By way of example, occlusion member 24 may extend between the distal end 16 of the first (proximal) hub 12 and a proximal end 32 of the second (distal) hub 30. A middle portion 44 of the occluding member 24 extends radially away from the longitudinal axis 18 when the device 10 is in an open configuration to form a wider diameter portion 46. In one example, the wider diameter portion 46 of the occlusion member 24 is generally centered or formed within a middle section 44 of occluding member 24, but alternatively, the wider diameter portion 46 may be off-center, such that it is located closer to one hub or the other as needed, depending, for example, on the particular use of the device 10 or the patient's unique anatomy. Preferably, the wider diameter portion 46 extends radially outwardly for a wide enough distance so that at least a portion of the occlusion member 24 is substantially adjacent to and/or abuts the vessel wall when the device 10 is deployed within the body vessel 42 as shown in FIG. 1 and FIG. 4. Preferably, at least part of the occlusion member 24, such as wider diameter portion 46, extends outwardly from the longitudinal axis 18 and achieves sufficient radial force against at least a portion of the vessel wall to hold and/or secure the device 10 in place so that risk of dislodgment and/or migration of the device 10 is substantially reduced or otherwise eliminated. The radially outward expansion of the device upon delivery and deployment is described in further detail below.

As further illustrated in FIGS. 1 and 4, the occlusion member 24 may taper radially inwardly from the wider diameter portion 46 to a more narrow diameter portions 48, 50 at each of the respective proximal and distal ends 26, 28. The more narrow diameter portions 48, 50 may be attached to one or both of the respective hubs 12, 30 by various attachment means, including welding, adhesive, glue, friction fit or similar attachment members (e.g., screws, threads) or alternatively, member 24 may be integrally formed with one or both of the hubs 12, 30. As illustrated in FIG. 1, the proximal and/or distal ends 26, 28 f the occlusion member 24 may be crimped down or otherwise contracted radially inwardly so that they can be held by, inserted into or otherwise retained within the respective proximal and distal hubs 12, 30.

Optionally, the occlusion member 24 and/or one or both of hubs 12, 30 may include anchoring members (not shown). The anchoring members may have any appropriate shape to keep the device 10 from moving or migrating within the body vessel 42. The anchoring members may include a plurality of barbs. Other examples of the anchoring members may include hooks, roughened surfaces or other similar structures that may engage the vessel wall and serve to prevent migration or dislodgement of the device 10 after deployment in the vessel 42.

One or both of the proximal and/or distal hubs 12, 30 may be formed at least partially from a radiopaque material, including, but not limited to stainless steel and/or gold, and/or radiopaque polymers or alloys or include one or more radiopaque markers to enhance visibility and placement during delivery, such as with a fluoroscope. In one non-limiting example, one or both of the hubs 12, 30 may be formed from a stainless steel cannula having a size in the range of about 0.300 mm to about 1.100 mm and preferably about 0.899 mm. As shown in FIGS. 1-4, one or both of the hubs 12, 30 and preferably the proximal hub 12 may include a rounded or smooth atraumatic tip 52 placed thereon. In one example, the atraumatic tip 52 is formed in a bullet-nose shape, but may also include other domed, smooth or rounded shapes. The atraumatic tip 52 may either be removably secured to the proximal hub 12 to aid in the placement and delivery of the device 10 in a desired location within a vessel or body lumen, after which time the tip 52 may be removed from the device 10 during and/or after deployment. Alternatively, the atraumatic tip 52 may be permanently secured to the proximal hub 12 such that it remains secured to the device 10 when it is deployed within a vessel 42, or, in yet another alternative, the proximal hub 12 itself may be atraumatically shaped, smooth and/or rounded. An atraumatically shaped hub 12 and/or atraumatic tip 52 may facilitate the ease of delivery and placement of the device 10 in tortuous anatomy while also reducing or eliminating vessel damage or injury.

The occluding member 24 may be a variety of structures including, but not limited to, one or more wires, coils, fabrics, fibers, flexible arcuate members, cages, screens, disks, walls and the like and may be constructed or formed from a single material or, alternatively, may be formed from a variety or combination of materials. In one example, at least a portion of occlusion member 24 may be formed of any suitable material that may be expanded, such as by mechanical expansion. In other examples, at least a portion of the occlusion member may be formed from any suitable material that will result in a self-opening or self-expanding device 10, such as shape memory material. Shape memory material that is heated (or cooled) above (or below) a transition temperature causes the material to undergo a phase transfoiiiiation such that the material returns to its "remembered" state. Thus, when the device 10 is deployed in a body vessel 42 having a particular temperature the device 10 will transform to the remembered (expanded) state within the vessel 42. To remove the device 10, it may be cooled (or, alternatively heated) to transform the material to a more malleable state, such that the device 10 can be more easily collapsed and pulled into a lumen of a catheter (re-sheathed) for removal. One shape memory alloy suitable for the present invention is Ni—Ti, also known as nitinol.

As shown in FIG. 1 and FIG. 4, occlusion member 24 is preferably formed of a woven mesh constructed of nitinol wire and a polyester fiber (polyethylene terephthalate commonly abbreviated PET, PETE) or referred to by the trade name Dacron®. The nitinol and polyester fiber mesh may be woven in any suitable combination or ratio, and in one example, the materials may be woven together in a ratio of 1:1 to form a mesh. The polyester fibers may act as a thrombogenic agent upon delivery and nesting of the device in a vessel 42 or body lumen. In an alternative embodiment, the occlusion member 24 may also be at least partially constructed of materials such as, but not limited to, nylon, rayon, biocompatible polyurethanes, polytetrafluoroethylene (known as PTFE or under the trade name Teflon®), and mixtures thereof.

In addition to a woven mesh of nitinol and a polyester fiber, the occlusion member 24 may also include or incorporate yet another material such as a coating, or, as part of the woven mesh, a connective tissue material including extracellular matrix (ECM) comprised of small intestinal submucosa (SIS). In one particular embodiment, the SIS may be used to temporarily adhere at least part of the occlusion member 24 to the walls of the body vessel 42 in which the device 10 is deployed. Since it may be desirable to only temporarily occlude the body vessel 42, when the device 10 is deployed in the body vessel, host cells of the wall may adhere to a portion of the device 10 but will not differentiate, allowing for later retrieval of the device 10 from the body vessel 42. However, in other applications where more permanent occlusion is desired, the device 10 may remain in place and the host cells of the wall may differentiate into the occlusion member 24, eventually replacing the SIS with the host cells of the body vessel 42.

When introduced into a body vessel 42, the device 10 may be oriented such that the proximal hub 12 is directed into a direction of blood flow as indicated by the arrow 54. Alternatively, the device may be introduced into the vessel in the opposite orientation such that the distal hub is oriented into a direction of blood flow, so in other words, the device may not be directionally dependent and can be introduced in a direction or orientation as necessary or desired depending on the procedure and/or location in the body. As previously mentioned, the device 10, and in particular at least a portion of occlusion member 24, is configured to prevent blood, emboli and other fluids from passing, thereby occluding the body vessel 42. As previously mentioned, the occlusion member 24 extends radially around the longitudinal axis 18 thus forming an interior volume or space 40. In one example, the interior space 40 may also include one or more additional structures (not shown) that form an additional barrier to fluid (such as blood). This may include, for example, one or more disk-like structures that lie substantially perpendicular to the longitudinal axis 18, springs, coils and/or a plurality fibers extending radially with respect to the axis 18. Any one or more of these additional occluding structures may be wholly contained within the volume 40, and in other examples, may lie outside the volume 40.

As best shown in FIGS. 2 and 3, the occlusion member 24 preferably collapses into a closed or radially inwardly contracted "delivery" configuration extending substantially along the longitudinal axis 18 during delivery of the device 10. For example, during delivery, the device 10 is preferably disposed within an outer delivery sheath 56 of a delivery assembly 100 which retains the device 10 in its radially contracted state during delivery. The outer delivery sheath 56 has a tubular body 58 extending from a proximal part 62 to a distal part 60. An inner member or catheter 64 is disposed within a sheath lumen 66 and is configured for axial movement relative to the outer sheath 56. The inner catheter 64 may be any type of elongate pushing member including, for example, a rod, stylet, or the like. The device 10 is removably coupled to a distal portion 68 of the inner catheter 64 and is deployable through the distal end 60 of the outer delivery sheath 56 by means of the relative axial movement of the inner catheter 64. In another example, the device 10 is not coupled to the inner catheter 64 but is merely pushed by the inner catheter 64 through the sheath 56 to a desired delivery location within a patient's body.

The device 10 may be removably coupled to the inner catheter 64 in various ways. For example, the distal portion 68 of the inner catheter 64 may be configured to engage at least one of the proximal and/or distal hubs 12, 30. In one example, the distal portion 68 may include a flexible threading coil for engaging the hub. Examples of a threading coil are disclosed in U.S. Pat. Nos. 5,725,534; 6,458,137 and/or 8,308,752; which are herein incorporated by reference. The device 10 may also be removeably coupled to the delivery assembly by other attachment mechanisms, including friction fit, fasteners or coupling appendages. As best shown in FIGS. 2 and 3, the proximal and/or distal ends and/or hubs 12, 30 may include a coupling mechanism 70. As illustrated, the coupling mechanism 70 is formed on distal hub 30 and may be any complimentary feature appropriate for engaging the inner catheter 64. The coupling mechanism 70 formed on the hub 30 may be a female opening, such as lumen 38 that may be threaded, an aperture, a slot, a recess, indentation, cut-out or the like, or alternatively, it may be a male structure, such as a flange, finger or projection that may, if desired, be threaded. The inner catheter 64 preferably includes a complimentary structure configured to engage with the coupling mechanism 70 on the hub 30. As FIG. 2 and Figure. 3 illustrates, the hub 30 includes a female opening 72, which is preferably formed as a recess or cut-out, that is shaped to receive a correspondingly shaped male projection 74 formed on the distal end 68 of the delivery catheter 64. As shown there, the male projection 74 can be generally described as having a "lollipop" shape which is received by a similarly shaped recess 72 formed in the hub 30 for capturing the lollipop 74. Of course, other corresponding shapes, including but not limited to square, rectangle, diamond or other shapes, forms or engageable structures formed on the hub 30 and on the catheter 64 may also be suitable which allow for the device 10 to be releasably secured to the delivery assembly 100.

As shown in more detail in FIGS. 7 and 8, the distal end 68 of the delivery catheter 64 comprises two "lollipop" shaped projections 74 extending therefrom. The two projections 74 may be diametrically opposed structures that are received by two correspondingly shaped recesses 72 formed in hub 30. The delivery catheter 64 and projections 74 may be formed from the same material or alternatively, the projections 74 may be formed of a material different from that of the catheter 64. In one example, the projections 74 are formed at least partially from a shape-memory alloy such as Nitinol. Thus, in a natural, relaxed state, the projections 74 flare radially outwardly at the distal-most end 75. Thus, when sheath 56 is retracted to expose the distal end 68 of the delivery catheter 64 as illustrated in FIG. 8, the projections 74 become radially outwardly flared such that the diameter formed between distal most ends 75 of projections 74 is greater than the diameter of the distal end 68 of delivery catheter 64. However, when the distal end 68 of the delivery catheter 64 is sheathed such that the sheath 56 covers the projections 74 as shown in FIGS. 3 and 7, the projections are pushed radially inwardly and urged into and "captured" by the correspondingly shaped recesses 72 formed in the hub. As illustrated in FIG. 7, the projections 74 remain captured within recesses 72, as the diameter between the distal-most ends 75 of the projections 74 is approximately the same as the diameter of the distal end 68 of the delivery catheter 64 when contained by the sheath. In use, retraction of the sheath 56 and subsequent outward flaring of projections 74 results in the projections 74 being separated from the recesses 72 as FIGS. 4 and 8 show. This allows the occlusion device 10 to be uncoupled from the delivery catheter 64 and deployed at a desired location within a vessel. If recapture, repositioning and/or removal of the device 10 is desired, re-sheathing of the distal end 68 of the delivery catheter 64 and of the device 10 (by pushing the sheath distally) urges the projections 74 radially inwardly and back into the recesses 72. With the projections 74 again captured by the recesses 72 and held in position within the sheath 56, the device 10 can be repositioned or retracted from the vessel 42.

As mentioned above, at least part of the occlusion member 24, such as wider diameter portion 46, extends radially outwardly from the longitudinal axis 18 when deployed such that it achieves sufficient radial force against at least a portion of the vessel wall 42. Such radial outward expansion of the device 10 upon deployment may be achieved in several ways. First, in one example, one or more resilient inner central elongate member(s) 76 extends between the proximal and distal hubs 12, 30 as shown in FIGS. 1 and 2. In the example shown, one central elongate member 76 may include a coiled member or spring that extends substantially along the longitudinal axis 18 and may optionally define a third lumen (not shown) between the first and second lumens 22 and 38 of the first and second hubs 12 and 30. A proximal end 78 of the spring 76 is secured to the proximal hub 12 and a distal end 80 of the spring 76 is secured to the distal hub 30. The proximal and distal ends 78, 80 of the spring 76 may be secured or adjoined to the respective hubs 12, 30 by various suitable attachment mechanisms, including welding, adhesives, friction fit, threading and/or other attachment members. The spring 76 is preferably biased in a contracted condition, such that when in a relaxed state (e.g., upon deployment of device 10 when the delivery sheath 56 is retracted and removed), the ends 78, 80 of the spring 76 contract towards each other, thus pulling the respective proximal and distal hubs 12, 30 towards each other. As such, the woven mesh of the occlusion member 24 extends radially outwardly at a location 44 that is generally centered between the respective hubs 12, 30 to form a substantially elliptical, ovoidal or egg-shape as illustrated in FIG. 1. In other words, the device 10 is generally self-expanding in that the central elongate member 76 contracts in its natural state when unsheathed, thus, promoting expansion of the occlusion member 24. The contraction of the central elongate member 76 may alone provide a self-expanding device 10. However, as previously mentioned, occlusion member 24 may also be constructed of a material having self-expanding properties (e.g. a woven mesh including nitinol, for example) which may radially self-expand in its natural relaxed state (e.g., when the delivery sheath 56 is retracted and removed). Thus, the self-expanding properties of central elongate member 76 alone and/or in combination with an occlusion member 24 that may also include self-expanding properties, facilitates radial self-expansion of the device 10 within a vessel.

The central elongate member 76 is also preferably longitudinally extensible such that it can be lengthened or stretched to facilitate a radially constricted delivery configuration of the device 10 as shown in FIG. 2. As such, the central elongate member 76 may be made from an appropriate resilient elastic material, including elastic polymer, stainless steel coil, a spring or any other appropriate flexible material that allows for longitudinal extension and contraction. When the device 10 is sheathed, the respective hubs 12 and 30 are extended away from each other in substantially opposing directions, thus longitudinally extending the central elongate member 76. As a result, the occlusion member 24 becomes radially inwardly contracted into a more slender delivery profile within the sheath 56. Withdrawal of the sheath 56 allows for the device 10 to radially outwardly self-expand within the vessel as shown in FIG. 1 and described in detail herein.

In alternative example, radial outward expansion of the occlusion device 10 may be achieved by providing two separate inner central elongate members 82, 84 coupled to each of the respective hubs 12, 30 as shown in FIGS. 3 and 4. The two central elongate members 82, 84 may be in the form of springs or coils, or alternatively, two correspondingly shaped threaded members, one of which is configured to receive the other in a threadedly engaging manner. The two elongate members 82, 84 preferably extend from each of the respective hubs 12, 30 towards each other to a point where their respective terminating ends are adjacent, and/or abut as shown in FIG. 3, and are capable of otherwise engaging each other as shown in FIG. 4. One of the elongate members, such as the distal member 84 illustrated in FIG. 4, may be rotated relative to the other elongate member 82. Such rotation may be achieved by rotation of the delivery catheter 64 by the user, which, in turn, causes rotation of the distal elongate member 84. Rotation of the distal elongate member 84 causes the two elongate members 82, 84 to engage each other (such as by one elongate member threadedly engaging the other elongate member) as illustrated in FIG. 4 which, in turn, pulls the respective hubs 12, 30 towards each other along the longitudinal axis. As the hubs 12, 30 are pulled towards each other, the woven mesh of the occlusion member 24 becomes extended radially outwardly at a location generally between the respective hubs 12, 30 to form a substantially elliptical, ovoidal or egg-shape as illustrated in FIG. 4. Similarly, rotation of distal elongate member 84 (such as by rotation of the catheter 64 in the opposite direction) causes the elongate members 82, 84 to unthread or otherwise disengage, thus moving the respective hubs 12, 30 longitudinally away from each other, such that the occlusion member 24 may be returned to a radially-inwardly constricted delivery configuration, as illustrated in FIG. 3 and, if necessary or desired, the device 10 may be recaptured or resheathed for adjustment and/or relocation of the device 10.

FIGS. 5 and 6 depict a delivery assembly 100 for introducing and retrieving an occlusion device 10 for occluding a body vessel 42. As shown, the delivery assembly 100 preferably includes an introducer sheath 102 that may be constructed from various flexible biocompatible materials such as polytetrafluoroethylene (PTFE), for percutaneously introducing an outer delivery sheath 56 into a body vessel 42. Of course, any other suitable material for the introducer sheath 102, or outer delivery sheath 56 may be used. The introducer sheath 102 may have any suitable size, for example, between about three-french to twelve-french, depending on the particular use and location of delivery and deployment. The introducer sheath 102 serves to allow the outer delivery sheath 56 and an inner member or catheter 64 to be percutaneously inserted to a desired location in the body cavity and/or vessel 42. The introducer sheath 102 receives the outer delivery sheath 56 and provides stability to the outer delivery sheath 56 as the outer delivery sheath 56 is advanced through the introducer sheath 102 to an occlusion area in the vasculature. As shown in FIGS. 5 and 6 the outer delivery sheath 56 has a hub 104 at its proximal end sized and configured to receive the inner catheter 64 and occlusion device 10 to be advanced therethrough. The size of the outer delivery sheath 56 may be based on the size of the body vessel 42 in which it percutaneously inserts, and the size of the device 10.

As shown, the assembly 100 may also include a wire guide 106 configured to be percutaneously inserted within the vasculature to guide the outer delivery sheath 56 to the occlusion area. The wire guide 106 provides the outer delivery sheath 56 with a path to follow as it is advanced within the body vessel 42. The size of the wire guide 106 may be based on the inside diameter of the outer delivery sheath 56 and the diameter of the target body vessel 42. In one non-limiting example, a wire having a size of about 0.018 inches to about 0.038 inches may be used.

When a distal end 108 of the outer delivery sheath 56 is at the desired location in the body vessel 42, the wire guide 106 is removed and the occlusion device 10, having a distal segment, end and/or hub 30 contacting, coupled to or otherwise releasably engaged with a distal portion 68 of the inner catheter 64, is inserted into the outer delivery sheath 56. The inner catheter 64 is advanced through the outer delivery sheath 56 for deployment of the device 10 through the distal end 108 to occlude the body vessel 42 during treatment of, for example, an aneurism. Preferably, the distal portion 68 of the inner catheter 64 includes a coupling mechanism as previously described which, in one non-limiting example, comprises a male coupling or protrusion 74 generally in the shape of a lollipop for releasably engaging or otherwise coupling to a correspondingly female-shaped opening, aperture, cut-out, slot and/or recess 72 formed in distal hub 30 of the device 10. Alternatively, the occlusion device 10 may be removably attached to the distal portion 68 of the inner catheter 64 in other known ways as previously mentioned, or in yet another example, the inner catheter 64 may not be attached to the device 10, but instead, the inner catheter 64 may simply be used to push the device 10 through delivery sheath 56 to its desired deployment location.

Following removal of the wire guide 106, the device 10 and inner catheter 64 are coaxially advanced through the outer delivery sheath 56 in order to position the device 10 to occlude the body vessel 42. The device 10 is guided through the outer delivery sheath 56 by the inner catheter 64, preferably from the hub 104, and exits from the distal end 108 of the outer delivery sheath 56 at a location within the vasculature where occlusion is desired. Likewise, the device 10 may be retrieved and/or repositioned by positioning the distal end 108 of the outer delivery sheath 56 adjacent the deployed device 10 in the vasculature. The inner catheter 64 is advanced through the outer delivery sheath 56 until the distal portion 68 protrudes from the distal end 108 of the outer delivery sheath 56. The distal portion 68 is coupled to a distal end or hub 30 of the device 10, such as by female recess 72 of coupling mechanism 70 capturing male protrusion 74, after which the inner catheter 64 is retracted proximally, drawing the device 10 into the outer delivery sheath 56 for repositioning and/or removal.

The occlusion device 10 and methods of use described herein provides easy, efficient, safe and dependable occlusion of a vessel and/or body lumen with improved stasis time and minimal risk of migration of the device 10. Advantageously, occlusion device 10 may be provided in a variety of sizes, shapes, lengths and combinations thereof, thus providing an immediately deliverable design for achieving occlusive properties for multiple uses and varying locations of placement, serving unique patient anatomies and shortening occlusion and stasis times. It is understood that the delivery assembly described above is merely one example of an assembly that may be used to deliver and deploy the occlusion device 10 in a body vessel. Of course, other apparatus, assemblies and systems may be used to deploy any embodiment of the occlusion device in a vessel, organ or body lumen as necessary or desired.

Throughout this specification, unless the context requires otherwise, the words "comprise" and "include" and variations such as "comprising" and "including" will be understood to imply the inclusion of an item or group of items, but not the exclusion of any other item or group items.

While various embodiments of the invention have been described, it will be apparent to those of ordinary skill in the art that many more embodiments and implementations are possible within the scope of the invention. Furthermore, although various indications have been given as to the scope of this invention, the invention is not limited to any one of these but may reside in two or more of these combined together. Accordingly, the invention is not to be restricted except in light of the attached claims and their equivalents.

The invention claimed is:

1. An occlusion device for occluding a body vessel comprising:
   a proximal end,
   a distal end spaced from the proximal end along a longitudinal axis,
   an occluding member disposed between the proximal end and distal end, the occluding member moveable between a radially-outwardly expanded configuration and a contracted configuration,
   a first biasing member disposed within the occluding member and having a first end adjoined to the proximal end of the device,
   a second biasing member disposed within the occluding member and having a first end adjoined to the distal end of the device, the second biasing member configured to releasably engage the first biasing member, such that in a first configuration the first and second biasing members are engaged and in a second configuration the first and second biasing members are disengaged.

2. The occlusion device of claim 1 wherein when proximal and distal ends are moved towards each other along the longitudinal axis, the occlusion member is moveable to the expanded configuration, and when proximal and distal ends are moved away from each other along the longitudinal axis, the occlusion member is moveable to the contracted configuration.

3. The occlusion device of claim 1 wherein at least one of the first and second biasing members is rotatable with respect to the other biasing member.

4. The occlusion device of claim 1 wherein each of the first and second biasing members is a helical coil.

5. The occlusion device of claim 1 wherein each of the first and second biasing members is threaded.

6. The occlusion device of claim 1 wherein the occluding member comprises a woven mesh.

7. The occlusion device of claim 6 wherein the self-expanding material and polyester fiber are woven in a ratio of at least one of 1:1; 1:2; 1:3; 1:4; 2:1; 3:1 and 4:1.

8. The occlusion device of claim 7 wherein the self-expanding material and polyester fiber are woven in a ratio of at least one of 1:1.

9. The occlusion device of claim 1 wherein at least one of the proximal and distal ends comprises a radiopaque material.

10. The occlusion device of claim 9 wherein each of the proximal and distal ends comprises a radiopaque material.

* * * * *